US006996995B2

(12) United States Patent
Voute et al.

(10) Patent No.: US 6,996,995 B2
(45) Date of Patent: *Feb. 14, 2006

(54) SYSTEMS AND METHODS FOR FREEZING AND STORING BIOPHARMACEUTICAL MATERIAL

(75) Inventors: Nicolas Voute, Cuges les Pins (FR); Maxime N. Lok, Marseilles (FR); Leonidas Cartwright Leonard, Mill Valley, CA (US); Timothy Gerard Hughes, Benicia, CA (US); Richard Wisniewski, San Mateo, CA (US)

(73) Assignee: Integrated Biosystems, Inc., Napa, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 10/724,793

(22) Filed: Dec. 1, 2003

(65) Prior Publication Data

US 2004/0129003 A1     Jul. 8, 2004

Related U.S. Application Data

(63) Continuation of application No. 10/254,036, filed on Sep. 23, 2002, now Pat. No. 6,698,213, and a continuation-in-part of application No. 09/905,488, filed on Jul. 13, 2001, now Pat. No. 6,453,683, which is a continuation-in-part of application No. 09/863,126, filed on May 22, 2001, now Pat. No. 6,635,414.

(60) Provisional application No. 60/334,622, filed on Nov. 1, 2001.

(51) Int. Cl.
*B65D 25/00* (2006.01)
*F25D 25/00* (2006.01)
*F25B 29/00* (2006.01)

(52) U.S. Cl. .................. 62/62; 62/378; 220/529.28; 165/63

(58) Field of Classification Search ............. 62/62, 62/66, 356, 340, 378; 220/592.28; 165/63
See application file for complete search history.

(56) References Cited

U.S. PATENT DOCUMENTS

| | | | |
|---|---|---|---|
| 2,662,520 A | 12/1953 | McMahon | 128/1 |
| 3,121,627 A | 2/1964 | Harris | 62/58 |
| 3,389,974 A | 6/1968 | Barattini et al. | 23/295 |
| 3,586,097 A * | 6/1971 | Bender et al. | 392/444 |
| 3,952,536 A | 4/1976 | Faust et al. | 62/293 |
| 3,959,981 A | 6/1976 | Anderson | 62/135 |
| 4,018,911 A | 4/1977 | Lionetti et al. | 424/101 |
| 4,030,314 A | 6/1977 | Strehler et al. | 62/65 |
| 4,090,374 A | 5/1978 | Faust et al. | 62/341 |
| 4,107,937 A | 8/1978 | Chimiel | 62/64 |
| 4,178,776 A | 12/1979 | Baldus et al. | 62/538 |
| 4,194,369 A | 3/1980 | Faust et al. | 62/371 |
| 4,251,995 A | 2/1981 | Pert et al. | 62/60 |
| 4,304,293 A | 12/1981 | Scheiwe et al. | 165/12 |
| 4,327,799 A | 5/1982 | Scheiwe et al. | 165/2 |
| 4,336,435 A | 6/1982 | Kashyap et al. | 219/10.55 |
| 4,469,227 A | 9/1984 | Faust | 206/527 |
| 4,473,739 A | 9/1984 | Scheiwe et al. | 219/302 |
| 4,486,389 A | 12/1984 | Darnell et al. | 422/307 |
| 4,490,982 A | 1/1985 | Christmas | 62/3 |
| 4,531,373 A | 7/1985 | Rubinsky | 62/63 |
| 4,565,073 A | 1/1986 | Lavender | 62/373 |
| 4,580,409 A | 4/1986 | Angelier et al. | 62/340 |
| 4,584,843 A | 4/1986 | Pronger, Jr. et al. | 62/123 |
| 4,596,120 A | 6/1986 | Knodel et al. | 62/59 |
| 4,609,036 A | 9/1986 | Schrader | 165/10 |
| 4,652,712 A | 3/1987 | Zeipel | 219/10.55 |
| 4,712,607 A | 12/1987 | Lindeman et al. | 165/30 |
| 4,779,358 A | 10/1988 | Atkinson et al. | 62/3 |
| 4,793,151 A | 12/1988 | Masel et al. | 62/306 |
| 4,801,777 A | 1/1989 | Auerbach | 219/10.55 |
| 4,843,827 A | 7/1989 | Peppers | 62/73 |
| 4,874,915 A | 10/1989 | Harms et al. | 219/10.55 |
| 4,893,670 A | 1/1990 | Joshi et al. | 165/40 |
| 4,954,679 A | 9/1990 | Harms et al. | 219/10.55 |
| 4,967,564 A | 11/1990 | Strasser | 62/47.1 |
| 4,971,737 A | 11/1990 | Infanti | 264/28 |
| 4,976,308 A | 12/1990 | Faghri | 165/10 |

| Patent No. | Date | Inventor | Class |
|---|---|---|---|
| 4,986,080 A | 1/1991 | Grigoli et al. | 62/75 |
| 5,005,371 A | 4/1991 | Yonezawa et al. | 62/238.6 |
| 5,022,149 A | 6/1991 | Abbott | 29/890.048 |
| 5,022,235 A | 6/1991 | Grissom | 62/529 |
| 5,029,634 A | 7/1991 | Hurner | 165/47 |
| 5,033,544 A | 7/1991 | Abbott | 165/184 |
| 5,054,548 A | 10/1991 | Zohler | 165/133 |
| 5,072,569 A | 12/1991 | VanTassel | 52/745 |
| 5,090,207 A | 2/1992 | Gilbertson et al. | 62/59 |
| 5,103,651 A | 4/1992 | Coelho et al. | 62/341 |
| 5,125,900 A | 6/1992 | Teves | 604/114 |
| 5,168,725 A | 12/1992 | Margolin | 62/457.9 |
| 5,176,197 A | 1/1993 | Hamaguchi et al. | 164/459 |
| 5,181,387 A | 1/1993 | Meckler | 62/59 |
| 5,205,128 A | 4/1993 | Richard | 62/63 |
| 5,212,957 A | 5/1993 | Ruff | 62/124 |
| 5,220,954 A | 6/1993 | Longardner et al. | 165/10 |
| 5,243,833 A | 9/1993 | Coelho et al. | 62/376 |
| 5,285,657 A | 2/1994 | Bacchi et al. | 62/457.9 |
| 5,332,034 A | 7/1994 | Chiang et al. | 165/184 |
| 5,374,436 A | 12/1994 | White et al. | 426/249 |
| 5,411,078 A | 5/1995 | Ares | 165/113 |
| 5,458,191 A | 10/1995 | Chiang et al. | 165/133 |
| 5,476,763 A | 12/1995 | Bacchi et al. | 435/284.1 |
| 5,520,885 A | 5/1996 | Coelho et al. | 422/101 |
| 5,524,706 A | 6/1996 | Nakamura et al. | 165/47 |
| 5,535,598 A | 7/1996 | Cothern et al. | 62/356 |
| 5,557,943 A | 9/1996 | Coelho et al. | 62/376 |
| 5,579,830 A | 12/1996 | Giammaruti | 165/104.27 |
| 5,582,856 A | 12/1996 | White et al. | 426/249 |
| 5,609,035 A | 3/1997 | Cothern et al. | 62/73 |
| 5,616,268 A | 4/1997 | Carr | 219/687 |
| 5,616,301 A * | 4/1997 | Moser et al. | 422/104 |
| 5,638,686 A | 6/1997 | Coelho et al. | 62/51.1 |
| 5,644,922 A | 7/1997 | Linden et al. | 62/51.1 |
| 5,689,961 A | 11/1997 | Cosman | 62/78 |
| 5,694,100 A | 12/1997 | Jacquet et al. | 62/373 |
| 5,750,658 A | 5/1998 | Coelho et al. | 530/382 |
| 5,779,974 A | 7/1998 | Kuzyk | 422/44 |
| 5,862,675 A | 1/1999 | Scaringe et al. | 62/193.3 |
| 5,863,715 A | 1/1999 | Rajotte et al. | 435/1.3 |
| 5,873,254 A | 2/1999 | Arav | 62/63 |
| 5,939,023 A | 8/1999 | Coelho et al. | 422/101 |
| 5,964,095 A | 10/1999 | Coelho et al. | 62/62 |
| 5,988,422 A | 11/1999 | Vallot | 220/62.22 |
| 5,996,427 A | 12/1999 | Masek et al. | 73/864.91 |
| 5,999,701 A | 12/1999 | Schmidt | 392/470 |
| 6,007,773 A | 12/1999 | Kuzyk | 422/44 |
| 6,065,294 A | 5/2000 | Hammerstedt et al. | 62/3.3 |
| 6,077,447 A | 6/2000 | Coelho et al. | 210/774 |
| 6,079,215 A | 6/2000 | Wisniewski | 62/46.1 |
| 6,098,410 A | 8/2000 | Horigane | 62/62 |
| 6,123,696 A | 9/2000 | Coelho et al. | 604/410 |
| 6,146,124 A | 11/2000 | Coelho et al. | 425/387.1 |
| 6,196,296 B1 | 3/2001 | Wisniewski et al. | 165/47 |
| 6,220,038 B1 | 4/2001 | Marsh et al. | 62/71 |
| 6,232,115 B1 | 5/2001 | Coelho et al. | 435/307.1 |
| 6,274,090 B1 | 8/2001 | Coelho et al. | 422/101 |
| 6,302,327 B1 | 10/2001 | Coelho et al. | 235/383 |
| 6,384,380 B1 | 5/2002 | Faries, Jr. et al. | 219/385 |
| 6,387,322 B1 | 5/2002 | Gallus | 422/38 |
| 6,393,860 B1 | 5/2002 | Heschel et al. | 62/376 |
| 6,453,683 B1 | 9/2002 | Wisniewski et al. | 62/75 |
| 6,605,213 B1 * | 8/2003 | Ammann et al. | 210/222 |

FOREIGN PATENT DOCUMENTS

| | | |
|---|---|---|
| DE | 4029216 | 3/1992 |
| EP | 0318924 | 6/1989 |
| EP | 0726080 A2 | 12/1995 |
| EP | 1 134 000 A2 | 9/2001 |
| FR | 2501057 | 10/1981 |
| WO | WO 97/18424 | 5/1997 |
| WO | WO 00/72902 | 12/2000 |

* cited by examiner

*Primary Examiner*—Chen Wen Jiang
(74) *Attorney, Agent, or Firm*—Heslin Rothenberg Farley & Mesiti P.C.; Nicholas Mesiti, Esq.; Victor A. Cardona, Esq.

(57) ABSTRACT

The present invention provides a system for freezing, thawing, and storing biopharmaceutical materials which includes a flexible container, a conduit, and a temperature control unit. The flexible container is adapted to receive a biopharmaceutical material therein for freezing, thawing, and storing. The container is formed of a first substantially flat sheet of flexible material joined together by a seam with a second substantially flat sheet of flexible material so as to lie substantially flat when empty. The container fully encloses an interior portion for receiving the biopharmaceutical material. Also, the container is configured to form a three dimensional shape when filled with the biopharmaceutical material, wherein the three dimensional shape has a first side and a second side opposite the first side. The conduit is connected to the flexible container with the outside of the container being in fluid communication with the interior portion via the conduit. The temperature control unit includes a first surface and a second surface facing the first surface and the temperature control unit is configured to receive the flexible container therein, when the container is filled with the biopharmaceutical material. The container conforms to the shape of the interior of the temperature control unit and the first side and the second side of the container contact the first surface and the second surface of the temperature control unit. The first surface and/or the second surface of temperature control unit include heat transfer surface(s).

23 Claims, 5 Drawing Sheets

SYSTEMS AND METHODS FOR FREEZING AND STORING BIOPHARMACEUTICAL MATERIAL

CROSS-REFERENCE TO RELATED APPLICATIONS

This application is a Continuation of U.S. Pat. No. 10/254,036, filed Sep. 23, 2002, now U.S. Pat. No. 6,698,213, which claims the benefit of U.S. Provisional application No. 60/334,622, filed Nov. 1, 2001, the disclosure of which is incorporated herein by reference. Also, U.S. Ser. No. 10/254,036 is a Continuation-in-Part of U.S. patent application Ser. No. 09/905,488, filed Jul. 13, 2001, entitled Cryopreservation System with Controlled Dendritic Freezing Front Velocity, now U.S. Pat. No. 6,453,683, issued Sep. 24, 2002, which is a continuation-in-part of U.S. patent application Ser. No. 09/863,126 filed May 22, 2001, now U.S. Pat. No. 6,635,414, issued Oct. 21, 2003, the disclosures all of which are incorporated herein by reference. Further, this application relates to U.S. patent application Ser. No. 10/254,025, filed Sep. 23, 2002, and U.S. patent application Ser. No. 10/744,967 filed Dec. 22, 2003, both of which are entitled Systems and Methods for Freezing, Storing and Thawing Biopharmaceutical Material, the entireties of which are incorporated herein by reference.

TECHNICAL FIELD

This invention relates, in general, to biopharmaceutical material, preservation methods and systems, and more particularly to a system and method for freezing, and/or storing biopharmaceutical materials.

BACKGROUND ART

Preservation of biopharmaceutical materials is important in the manufacture, storage, sale and use of such materials. For example, biopharmaceutical materials are often preserved by freezing between processing steps and during storage. Similarly, biopharmaceutical materials are often frozen during transportation between manufacturing locations.

Currently, preservation of biopharmaceutical material often involves placing a container containing liquid biopharmaceutical material in a cabinet freezer, chest freezer or walk-in freezer and allowing the biopharmaceutical material to freeze. Specifically, the container is often placed on a shelf in the cabinet freezer, chest freezer or walk-in freezer and the biopharmaceutical material is allowed to freeze. These containers may be stainless-steel vessels, plastic bottles or carboys, or plastic flexible containers. They are typically filled with a specified volume to allow for freezing and expansion and then transferred into the freezers at temperatures typically ranging from negative 20 degrees Celsius to negative 70 degrees Celsius or below.

To ensure efficient use of available space inside the freezer, containers are placed alongside one another and sometimes are stacked into an array with varied spatial regularity. Under these conditions, cooling of the biopharmaceutical solution occurs at different rates depending on the exposure of each container to the surrounding cold air, and the extent to which that container is shielded by neighboring containers. For example, containers placed close to the cooling source or those on the outside of an array of containers would be cooled more rapidly than those further away from the cooling source and/or situated at the interior of the array.

In general, adjacent placement of multiple containers in a freezer creates thermal differences from container to container. The freezing rate and product quality then depend on the actual freezer load, space between the containers, and air movement in the freezer. This results in a different thermal history for the contents of the containers depending on their location in a freezer, for example. Also, the use of different containers for individual portions of a single batch of biopharmaceutical material may cause different results for portions of the same batch due to different thermal histories resulting from freezing in a multiple container freezer, particularly if the storage arrangement is haphazard and random. Another consequence of obtaining a range of freezing times is that certain containers may freeze so slowly that the target solute can no longer be captured within the ice phase, but remains in a progressively smaller liquid phase. This phenomenon is referred to as "cyroconcentration." In some cases such cyroconcentration could result in pH change, unfolding, aggregation, or precipitation of the biopharmaceutical product, thus resulting in product loss.

Disposable containers such as plastic flexible containers or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic flexible containers, during freezing, thawing, or transportation of these containers often result in damage thereof, due, for example, to shock, abrasion, impact, or other mishandling events arising from operator errors or inadequate protection of the flexible containers in use.

Thus, there is a need for systems and methods for freezing, storing, and thawing of biopharmaceutical materials that are controlled, do not result in loss of biopharmaceutical material, but instead create conditions conducive to preserving the biopharmaceutical material in a uniform, repeatable fashion in a protected environment.

SUMMARY OF THE INVENTION

The present invention provides, in a first aspect, a system for freezing, thawing, and storing a biopharmaceutical material, which includes a flexible container adapted to receive liquid biopharmaceutical material therein for freezing, thawing, and storing. The container includes a first substantially trapezoidal portion attached to a second substantially trapezoidal portion.

The present invention provides, in a second aspect, a system for freezing, thawing, and storing biopharmaceutical material which includes a flexible container, a conduit and a temperature control unit. The flexible container is adapted to receive a liquid biopharmaceutical material therein for freezing and storing. The container may be formed of a first substantially flat sheet of flexible material joined together by a seam with a second substantially flat sheet of flexible material so as to lie substantially flat when empty and wherein the container fully encloses an interior portion for receiving the biopharmaceutical material. Also, the container is configured to form a three-dimensional shape when filled with the biopharmaceutical material wherein the three dimensional shape has a first side and a second side opposite the first side. The conduit is connected to the flexible container to allow the outside of the container to be in fluid communication with the interior portion of such conduit.

The temperature control unit includes a first surface and a second surface facing the first surface. Also, the temperature control unit is configured to receive the flexible container therein, when the container is filled with the biopharmaceutical material. The container conforms to the shape of the interior of the temperature control unit and the first side and the second side of the container contact the first surface and the second surface of the temperature control unit. The first and/or second surfaces of the temperature control unit include a heat transfer surface(s).

The present invention provides, in a third aspect, a system for freezing, thawing, and storing a biopharmaceutical material which includes a flexible container and a temperature control unit. The flexible container is adapted to receive liquid biopharmaceutical material therein for freezing, thawing, and storing. Also, the container is configured to conform to a shape of an interior of a temperature control unit, in response to the container being substantially filled with the biopharmaceutical material. The temperature control unit includes at least one heat transfer surface and at least one movable wall adapted to compress the container to inhibit a clearance between the container and the at least one heat transfer surface. Further, the at least one moveable wall may include the at least one heat transfer surface or the at least one moveable wall may provide support for the flexible container without having heat transfer capabilities.

The present invention provides, in a fourth aspect, a system for freezing, thawing, and storing a biopharmaceutical material, which includes a container adapted to receive biopharmaceutical therein for freezing. The container is configured to conform to a shape of an interior of a temperature control unit, when the container is substantially filled with the biopharmaceutical material. Also, the container includes a first portion attached to a second portion wherein the first portion and the second portion are flat. Furthermore, the portions may be substantially trapezoidal portions, substantially triangular portions, substantially rectangular portions, substantially parallelepipedic portions, substantially elliptic portions, substantially semicircular portions, or substantially parabolic portions. The interior of the temperature control unit may have the same shape as the aforementioned containers, when the containers are substantially filled.

The present invention provides, in a fifth aspect, a method for freezing, thawing, and storing a biopharmaceutical material which includes connecting a first flat substantially trapezoidal portion to a second flat substantially trapezoidal portion to form a container adapted to contain the biopharmaceutical material for freezing and adapted to conform to a shape of an interior of a temperature control unit.

The present invention provides, in a sixth aspect, a method for freezing and storing a biopharmaceutical material. The method includes providing a container adapted to contain the biopharmaceutical material for freezing and adapting the container to conform to a shape of an interior of a temperature control unit. The method further includes compressing the container, when it is received in the interior of the temperature control unit, to inhibit a clearance between the container and at least one heat transfer surface of the temperature control unit.

The present invention provides, in a seventh aspect a method for freezing, thawing, and storing a biopharmaceutical material. The method includes joining a first substantially flat sheet of flexible material by a seam with a second substantially flat sheet of flexible material to form a flexible container adapted to receive a biopharmaceutical therein for freezing, thawing, and storing. An interior portion of the container is fully enclosed for receiving the biopharmaceutical material by the joining of the first substantially flat sheet of flexible material with the second substantially flat sheet of flexible material. A three-dimensional shape is formed with the container by filling the container with the biopharmaceutical material wherein the three-dimensional shape has a first side and a second side opposite the first side. A conduit may be connected to the flexible material wherein the outside of the container is in fluid communication with the interior portion via the conduit. The container may be received in a temperature control unit having a first surface and second surface facing the first surface and the shape of the container may conform to an interior of the temperature control unit. The first surface and the second surface of the temperature control unit may contact the first side and the second side of the container wherein the first surface and/or the second surface may include a heat transfer surface.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION OF ONE PREFERRED EMBODIMENT OF THE INVENTION

In accordance with the principles of the present invention, systems and methods of preserving and storing biopharmaceutical materials are provided.

In an exemplary embodiment depicted in FIGS. 1–5, portions of a system for cooling, thawing, preserving and storing biopharmaceutical materials are shown. This system may include a sterile container, such as a flexible container 10, adapted to contain the biopharmaceutical materials and configured to conform to a shape of an interior of a temperature control unit, such as a heat exchanger 20.

Heat exchanger 20 is configured to be operatively coupled to a temperature regulating unit 27 for controlling fluid flow through a conductive medium such as heat transfer plates 40 of heat exchanger 20 to control the temperature of an interior 25 of heat exchanger 20. A controller 500 allows a user to control temperature regulating unit 27 to control heating and/or cooling of the conductive medium, such as plates 40, to cause freezing or thawing, for example, of biopharmaceutical materials in a container, such as flexible container 10, when it is inserted into interior 25 of heat exchanger 20. One example of a heat exchanger is described in co-owned U.S. patent application Ser. No. 09/905,488 filed Jul. 13, 2001, and co-owned U.S. patent application Ser. No. 09/863, 126, filed May 22, 2001, the entireties of each of which are hereby incorporated herein by reference. The cooling systems described in the aforementioned applications, and freezing and/or thawing techniques described therein, may be used in conjunction with the systems and methods of freezing and storing biopharmaceutical materials of the present invention. Specifically, the coolers or heat exchangers described in these applications may be configured to incorporate and/or receive the containers for storing biopharmaceutical materials described herein and any associated structures.

Figure 1:
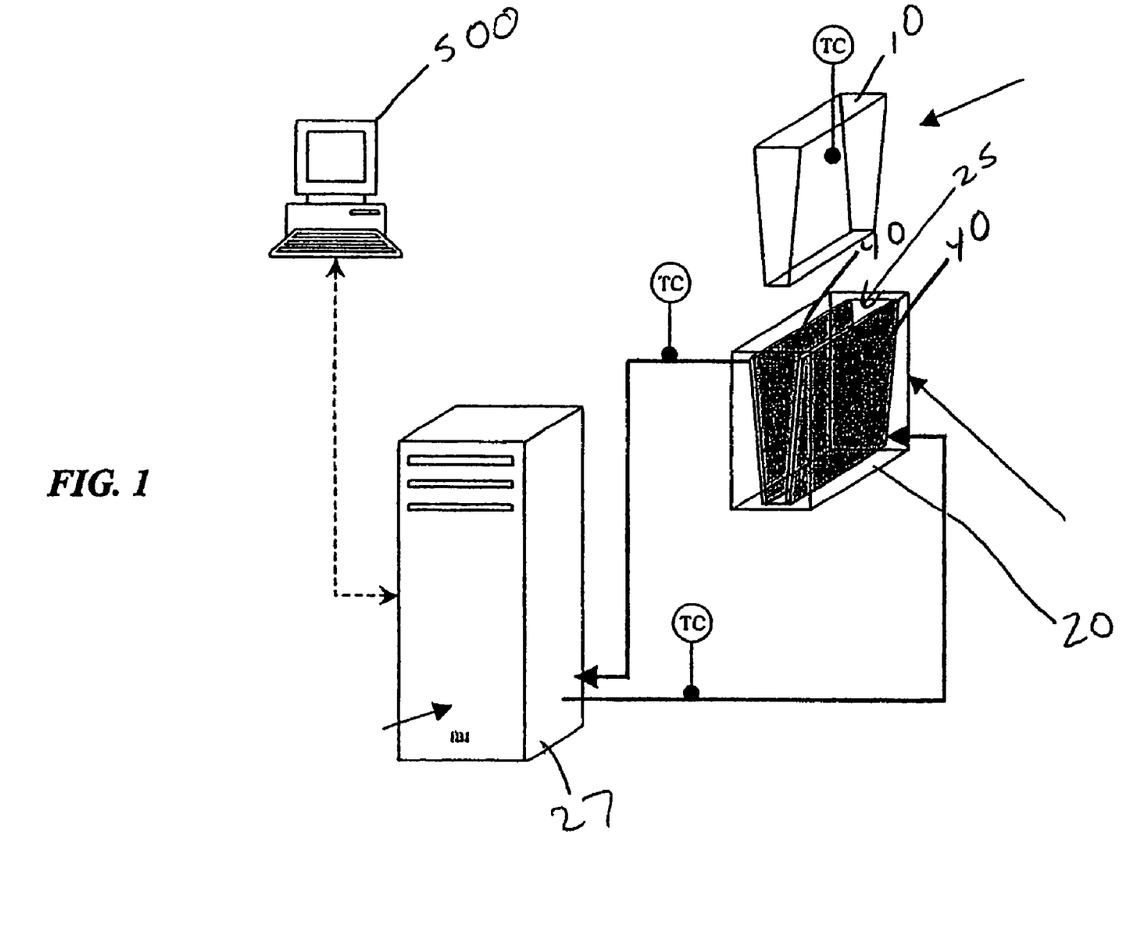
FIG. 1 is block diagram of a system for freezing, thawing, and storing biopharmaceutical material, in accordance with the present invention.
Figure 2:
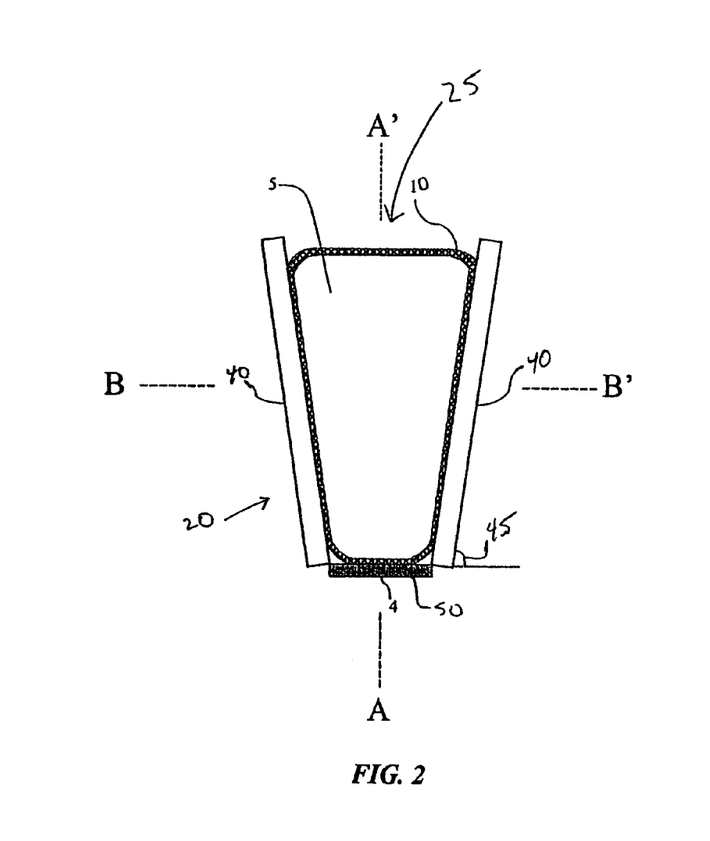
FIG. 2 is a side cross-sectional view of a temperature control unit of the system of FIG. 1 having a container therein.

As depicted in FIG. 2, heat transfer plates 40 may be arranged non-parallel relative to one another and may be arranged relative to bottom wall 50 such that interior 25 comprises a tapered space with a smaller distance between heat transfer plates 40 at their bottom ends than at their top ends. This tapered slot provides a larger cross-section at its top extent than its lower extent thus providing a head pressure which also serves to promote contact of flexible container 10 with heat transfer plates 40. Also, the tapered arrangement of plates 40 is favorable since it provides means for directing the volumetric ice expansion in an upward vertical direction. Because the distance between plates 40 increases along a vertical axis of flexible container 10, the time required for solidification for ends to meet at a mid-point between the plates increases along the vertical axis. Thus, the volumetric ice expansion is not constrained because there is always a liquid or air cavity above. Such an arrangement inhibits uncontrolled volumetric ice expansion, which can place stresses on walls of containers, such as flexible containers, that may result in ruptures of the containers and loss of biopharmaceutical materials.

Flexible container 10 may be formed of a laminated film which includes several layers and may have an interior volume ranging from 0.02–1000 liters, for example. More preferably, flexible container 10 may have a volume between 0.5–250 liters and most preferably, flexible container 10 may have a volume between 0.100–0.5 liters. For example, a biocompatible product-contacting layer may be formed of a low density polyethylene, very low density polyethylene, ethylene vinyl acetate copolymer, polyester, polyamide, polyvinylchloride, polypropylene, polyfluoroethylene, polyvinylidenefluoride, polyurethane, fluoroethylenepropylene, ethylene-vinyl alcohol copolymer, polytetrafluoroethylene, polypropylenes, and copolymers, mixtures or laminates that comprise the above. A gas and water vapor barrier layer may be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with cold conditions and may be able to withstand ionization for sterilization purposes. One example of materials useful for formulation of flexible container 10 is described in U.S. Pat. No. 5,988,442 to Vallot, which is hereby incorporated herein by reference.

Figure 3:
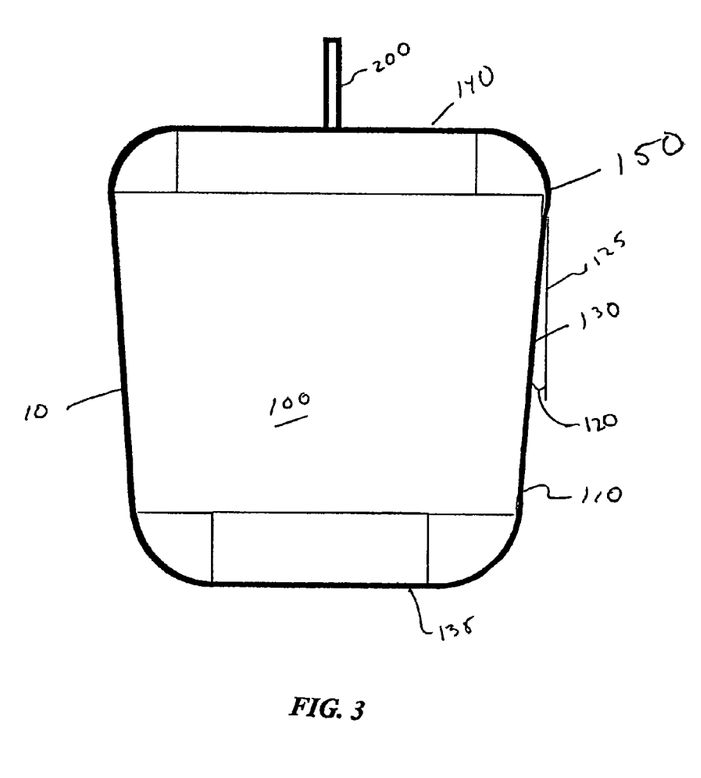
FIG. 3 is a side elevational view of a flexible container for thawing, storing, and freezing biopharmaceutical materials useable in the system of FIG. 1 prior to assembly thereof.

Flexible container 10 may be formed by welding the edges of two flat sheets of the materials described above to one another to form a seam and to enclose an interior portion therebetween. For example, two such flat sheets may be formed in a substantially trapezoidal shape thus resulting in the welding of the edges thereof forming a bag of a substantially trapezoidal shape, as best depicted in FIG. 3. For example, a top trapezoidal portion 100 might be welded to a bottom identically sized trapezoidal portion (not shown) at a seam 110 resulting in a flat bag having a trapezoidal shape. Further the trapezoidal portions may be formed such that, when arranged flat one atop the other, an angle 120 between a side 130 of flexible container 10 and an indicator line 125 substantially perpendicular to a bottom side 135 and/or a top side 140 of flexible container 10 may be complimentary to an angle 45 (FIG. 2) between one of heat transfer plates 40 (FIG. 2) and a bottom side 50 (FIG. 2) of heat exchanger 20. For example, angle 45 may be in a range from 0.001 degree to 45 degrees, more preferred being between 0.1 degree and 20 degrees and most preferred being between 0.5 degree and 15 degrees.

Figure 7:
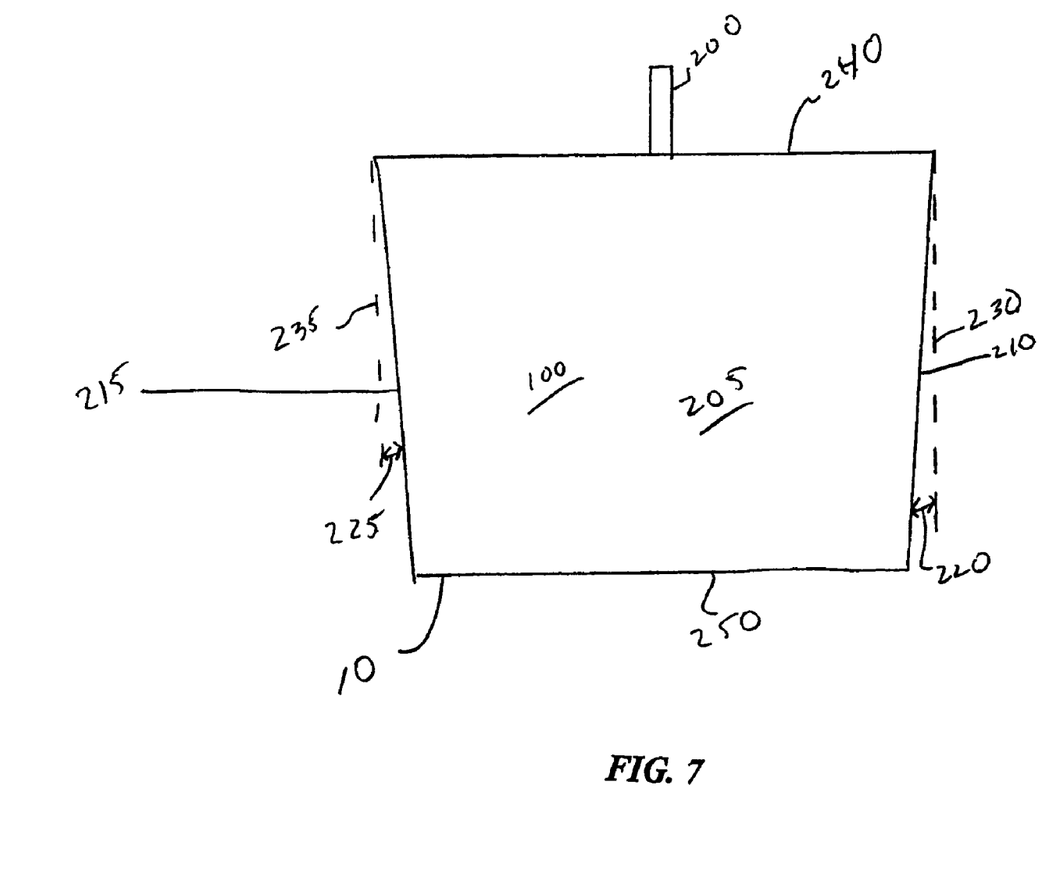
FIG. 7 is a side elevational view of the container of FIG. 3 when substantially filled with biopharmaceutical materials and compressed in the interior of the temperature control unit of the system of FIG. 1.

Further, flexible container 10 may form a prismatic shape (e.g., an equilateral prismatic shape) in response to being filled with the biopharmaceutical material and being supported by the tapered slot formed by two non-parallel heat transfer plates 40. Also, when flexible container 10 is substantially filled with a liquid biopharmaceutical material, two opposite sides of flexible container 10 crossed at their mid-point by seam 110 may be trapezoids, e.g. a first trapezoidal side 205 and a second trapezoidal side (not shown), as depicted in FIG. 7. Also, a substantially rectangular lateral side 210 adjacent to first trapezoidal side 205 may be at an angle 220 to an indicator line 230 substantially perpendicular to a top side 240 and/or a bottom side 250 of flexible container 10. A second substantially rectangular lateral side 215 adjacent to first trapezoidal side 205 may be at a second angle 225 relative to a second indicator line 235 substantially perpendicular to top side 240 and/or bottom side 250. Angle 220 and angle 225 may be substantially equivalent to angle 120 formed when flexible container 10 is flat and top trapezoidal portion 100 is arranged flat atop the bottom trapezoidal portion (not shown), as depicted in FIG. 3. Moreover, a bag adapted to receive a biopharmaceutical material could be formed of two similarly sized flat sheets of other shapes welded to each other, e.g., rectangular, triangular, parallelepipedic, elliptic, semicircular, or parabolic shaped sheets. For example, a bag formed of two similarly sized flat rectangular sheets would have two opposite rectangular sides, when substantially filled with the biopharmaceutical material and supported by two parallel heat transfer plates 40.

The formation of flexible container 10 in a substantially prismatic shape, when substantially filled with biopharmaceutical material, for example, as described above, allows flexible container 10 to be received in, and substantially conform to the shape of interior 25 of heat exchanger 20, as depicted in FIGS. 1–2 and 4–5. For example, seam 110 (FIG. 3) connecting top side 100 with bottom side (not shown) of flexible container 10 may be received in interior 25 such that seam 110 abuts one of side walls 60 of heat exchanger 40. Further, in response to flexible container 10 being filled with the biopharmaceutical material, seam 110 may be located in a plane substantially perpendicular to one or both of side walls 60. This configuration allows flexible container 10 to substantially contact heat transfer plates 40. Also, side walls 60 may include depressions on interior sides thereof to receive seams 110. Such depressions also promote contact between flexible container 10 and heat transfer plates 40. Such contact is desirable since air between flexible container 10 and heat transfer plates 40 may act as an insulator therebetween which could inhibit or delay cooling or heating of the biopharmaceutical material in flexible container 10.

Further, the formation of flexible container 10 using two trapezoidal portions allows it to substantially conform to the tapered slot of interior 25 and to inhibit deformation of the side ends of flexible container 10, when flexible container 10 is filled with the biopharmaceutical material and received in interior 25. Tapered or prismatic shaped flexible containers may be preferred to square or rectangular flat flexible containers having rounded corners wherein such rounded corners may not contact heat transfer plates, such as heat transfer plates 40, when received in a device such as heat exchanger 20. Such rounded corners may result in a low ratio of contact surface area to volume. Thus, less direct contact between flexible container 10 and the heat transfer plates and uneven heating or cooling of the biopharmaceutical material held in these flexible containers may result. Further, heating or cooling of the biopharmaceutical material in such square or rectangular flexible containers may be less efficient than flexible container 10 due to the greater contact of flexible container 10 with heat transfer plates 40. Specifically, pockets of air between a bag and heat transfer plates result in less efficient heat transfer since such heat transfer is done by natural convection instead of conduction. The heat transfer plates must cool or heat the air which then cools or heats the bag and biopharmaceutical material as opposed to the heat transfer plates directly cooling the bag and the biopharmaceutical material contained therein. It is thus desirable for the bag to be in direct contact with the heat transfer plates to promote conductive heat transfer, which is more efficient in this case than convective heat transfer of the air, bag, and biopharmaceutical materials. Further, the formation of flexible container 10 to conform to the tapered slot of interior 25 promotes such conductive heat transfer.

Figure 4:
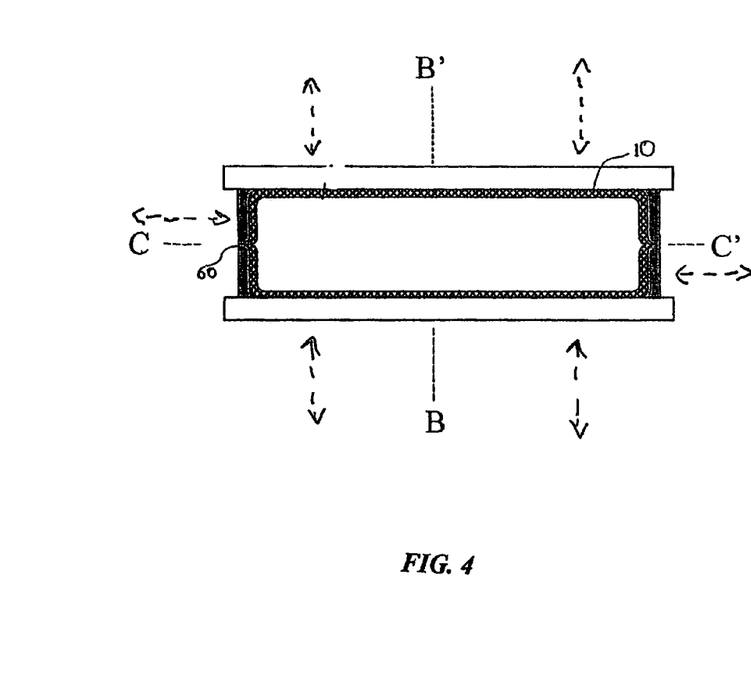
FIG. 4 is a top cross-sectional view of the temperature control unit of FIG. 1.
Figure 5:
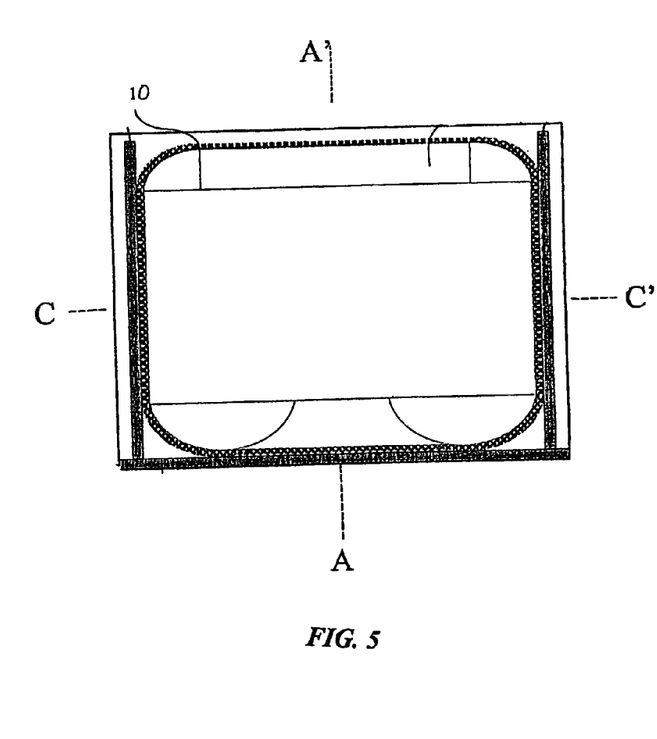
FIG. 5 is a front cross-sectional view of the temperature control unit of FIG. 1.

In an alternate embodiment and as shown in FIG. 4, one or both of side walls 60 of heat exchanger 20 may be moveable. Specifically, walls 60 may be moveable toward or away from one another between heat transfer plates 40. The movability of one or more of side walls 60 allows flexible container 10 to be compressed. The compressing promotes contact of flexible container 10 with heat transfer plates 40 while inhibiting any space or clearance between flexible container 10 and heat transfer plates 40. Specifically, such compression may force the biopharmaceutical material or other liquid in flexible container 10 to occupy any voids between heat transfer plates 40 and flexible container 10. For example, such pressure may cause the biopharmaceutical material to occupy such voids or be forced up due to the tapered slot shape of interior 25. Alternatively, side walls 60 may be fixed, whereas heat transfer plates 40 may be moveable towards or away from one another. Also, the required compression may be achieved by one of side walls 60 and/or one of heat transfer plates 40 being moveable. Also, it will be understood by those skilled in the art that side walls 60 may be maintained at particular positions relative to one another and relative to heat transfer plates 40 via pins, notches, or grooves in heat transfer plates 40 or bottom side 50 of heat exchanger 20. Side walls 60 and/or heat transfer plates 40 may be moveably, fixedly, and/or releasably attached to each other and/or bottom wall 50. Further, the ability of side walls 60 and/or heat transfer plates 40 to move could facilitate removal of flexible container 10 received therein. For example, by retracting walls 60 and/or plates 40 removal of frozen biopharmaceutical material held in heat exchanger 20 may be facilitated. Also, it will also be understood by those skilled in the art that side walls 60 and/or bottom 50 could also be adapted to provide cooling and/or heating to flexible container 10 via circulation of heat transfer fluids in coils therein or other means, as will be understood by those skilled in the art. Compression of flexible container 10 by one or more of side walls 60 and/or heat transfer plates 40 may cause flexible container 10 to form the prismatic shape described above, for example, thus promoting contact between flexible container 10 and heat transfer plates 40. Moreover, the shape of side walls 60 may match profiles of flexible flexible containers of other shapes when compressed. Also, side walls 60 and/or heat transfer plates 40 may be formed of a high thermal conductivity material, for example, stainless steel or aluminum.

As depicted in FIG. 3, flexible container 10 may include an inlet port 200 to allow biopharmaceutical materials to be inserted into the interior (not shown) of flexible container 10 and to be removed therefrom. Inlet port 200 may include a conduit or tube, for example, which may be integral to flexible container 10 or which may be connected to inlet port 200 using a fitting placed within the inlet port. Fittings such as those described in U.S. Pat. No. 6,186,932, the specification of which is incorporated herein by reference, may be used for the connection of such tubes. Also, fittings which can maintain the sterility of the contents of the container or bag may preferably be used. The fittings may be configured in different shapes, such as straight fittings and/or angled fittings including ninety (90) degree elbows, if desired. Inlet port 200 may include a filter (not shown) to filter any biopharmaceutical material. Flexible container 10 may also be emptied by turning flexible container 10 upside down and allowing the contents to drain. Also, a rigid or semi rigid holder (not shown) may be attached to flexible container 10 to facilitate carrying and/or storage of flexible container 10.

Moreover, although the container is described herein as a flexible container or bag, the container may be made of a semi-rigid material. Such material may be used to construct a container which is shaped to conform to the interior of heat exchanger 20. Preferably, the container whether formed of a flexible or semi-rigid material, includes surfaces which contact the interior surfaces of a heat exchanger 20 so that there is direct contact between the cooled (or heated in a thawing process) surfaces of heat exchanger 20 and the outer surfaces of the container containing biopharmaceutical materials.

After the biopharmaceutical material is frozen (e.g., to negative 20EC or below) or its temperature otherwise regulated in flexible container 10 in a temperature control unit, such as heat exchanger 20, flexible container 10 may be removed therefrom and placed in a freezer for storage or the biopharmaceutical material may be removed from flexible container 10 and utilized.

Figure 6:
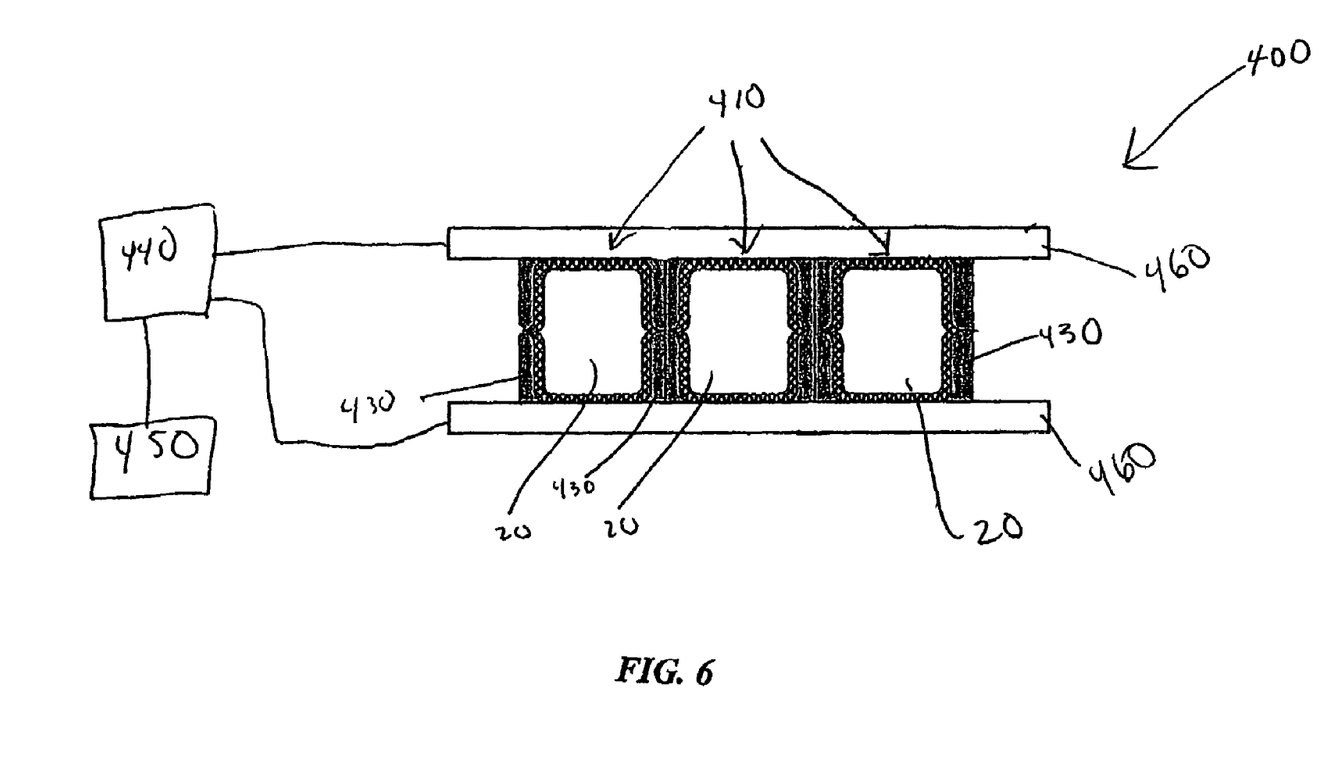
FIG. 6 is a block diagram of a system for regulating the temperature of a plurality of flexible containers for holding biopharmaceutical material.

In a further embodiment of the present invention, a heat exchanger 400 may include a plurality of receiving interior portions 410 for receiving a plurality of flexible container 10 adapted to contain biopharmaceutical material, as depicted in FIG. 6. Each receiving interior portion 410 may include a plurality of moveable walls 430 for compressing flexible container 10. Heat exchanger 400 also may include one or more heat transfer plates 460 for regulating a temperature of flexible container 10 and therefore the contents thereof. Heat exchanger 400 is coupled to a temperature regulating unit 440 for regulating temperatures of plates 460 wherein temperature regulating unit 440 is controlled by a controller 450, programmable by a user.

A typical process of preserving biopharmaceutical material is described as follows. Liquid biopharmaceutical material is inserted through port 200 into flexible container 10. Flexible container 10 is then inserted into heat exchanger 20, as shown in FIGS. 1, 2, 4 and 5, where the biopharmaceutical contents are cooled and frozen (e.g., at a sub-zero temperature) in a controlled manner such that the freeze rate is controlled within upper and lower limits, as described in U.S. patent application Ser. No. 09/905,488 for example, to prevent or inhibit cryoconcentration of the biopharmaceutical material, thereby preventing undesirable degradation of the biopharmaceutical material. Alternatively, flexible container 10 may be inserted into heat exchanger 20 before the biopharmaceutical material is inserted into flexible container 10. After the biopharmaceutical material in flexible container 10 is frozen, flexible container 10 may be removed from heat exchanger 20 and placed in a large freezer, for example, a walk-in freezer having an interior air temperature of about negative 20EC or lower, as is typically present in pharmaceutical production plants or large medical institutions (e.g., hospitals). The biopharmaceutical material may be removed from the walk-in freezer and inserted in a temperature control unit, such as heat exchanger 20, to be thawed, when it is desired to utilize or further process the biopharmaceutical material. It will be further understood by those skilled in the art that modifications may be made to the specific examples described herein and the steps for performing the method for preserving the biopharmaceutical material.

Also, it will be understood to one skilled in the art that the flexible containers described herein may be adapted for use in vessels, containers, temperature control units, and/or heat exchangers of various shapes or sizes. For example, the flexible containers could be formed in triangular, conical, cylindrical, pyramidal frustum or conical frustum shapes. Further, the temperature control units, e.g., heat exchanger 20, may be formed to have interior portions of various shapes which may be adapted to receive containers or flexible containers of various shapes or sizes. Also, temperature control units of various types may be utilized in addition to heat exchanger 20. For example, blast freezing units might also be utilized to control the temperature of the contents of flexible containers such as flexible container 10. Additionally, cryogenic fluid may be sprayed on flexible container 10 for cooling or warm fluid may be sprayed thereon for heating thereof. Moreover, the temperature control units may be of various shapes or sizes to accommodate containers or flexible containers of various shapes or sizes. The temperature control unit could also be adapted to heat and/or cool interior portions thereof to various temperatures. Also, the temperature control units could include any number of movable walls to compress flexible containers held therein. Furthermore, these flexible containers, containers, temperature control units, blast freezing units, and/or heat exchangers may be adapted for utilization with materials other than biopharmaceutical materials.

Further, although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A container or freezing, storing and thawing a biopharmaceutical material, which is receivable in a temperature control unit, said container comprising:
   a container material having an exterior contact area and an interior configured to receive the biopharmaceutical material therein for freezing, storing and thawing;
   said container material connectable to a support member having a handle, said support member configured to support a weight of said container material in response to said support member being connected to said container material, said support member being received on a support structure in the temperature control unit and said interior receiving the biopharmaceutical material; and
   said support member being configured to support said container material within the temperature control unit allow said contact area to contact a heat transfer surface separate from said support member to allow heat transfer between said heat transfer surface and the biopharmaceutical material.

2. The container of claim 1 wherein said support member is configured to support the container within a channel of a transportation cart in response to said support member being received on a support structure of the transportation cart.

3. The container of claim 1 wherein said container material forms a biopharmaceutical container which comprises a vertical dimension greater than a horizontal dimension in response to said biopharmaceutical container being received in an interior of the temperature control unit.

4. The container of claim 1 further comprising a port to provide fluid communication between said interior of said container material and an exterior of said container material.

5. The container of claim 1 wherein said handle is configured to allow a user to manipulate said container material holding the biopharmaceutical material.

6. The container of claim 1 wherein said support member is configured to support said container material to allow said contact area to be exposed to a contacting surface moveable relative to said container material to cause the heat transfer surface to contact said container material.

7. The container of claim 1 wherein said support member comprises at least one of a holder and a frame top to support said container material on the support structure of the temperature control unit.

8. The container of claim 1 wherein said container material comprises at least one of a flexible material and a semi-rigid material.

9. A system for freezing, storing and thawing a biopharmaceutical material, said system comprising:
   a container having an exterior contact area and being configured to receive the biopharmaceutical material therein;
   a support member having a handle, said support member connectable to said container and configured to be received on at least one support structure within a temperature control unit, said support member configured to support a weight of said container to allow a heat transfer surface of the temperature control unit, separate from the support member, to contact said contact area to allow heat transfer between the heat transfer surface and the biopharmaceutical material in response to said support member being connected to the container, said support member being received on the at least one support structure in the temperature control unit and the biopharmaceutical material being received in said container.

10. The system of claim 9 wherein said support member is configured to support said container on at least one of a plurality of channel supports of a transportation cart and a plurality of rails of a walk-in freezer.

11. The system of claim 9 wherein said container comprises at least one aperture, said support member further comprises at least one post projecting from said support member, and wherein said at least one aperture is adapted to receive said at least one post to allow said support member to support said container.

12. The system of claim 11 wherein said support member further comprises a capture member for sandwiching said container between said capture member and said support member about said at least one post.

13. The system of claim 11 further comprising a capture member pivotally connected to said support member, wherein said capture member comprises at least one opening configured to receive said at least one post to connect said capture member, said container, and said at least one post.

14. The system of claim 9 wherein said support member is configured to support said container in the temperature control unit and in a storage unit.

15. The system of claim 14 wherein said container comprises a thickness and at least one of a receiving portion of said temperature control unit and a receiving portion of said storage unit comprise at least one channel and said thickness is dimensioned to allow said container to be received in said at least one channel.

16. The system of claim 9 wherein said container is compressible within a width dimension of said support member.

17. The system of claim 9 wherein said container comprises at least one of a flexible container and a semi-rigid container.

18. A method for freezing, storing and thawing a biopharmaceutical material, the method comprising:
providing a container having an exterior contact area and an interior configured to contain the biopharmaceutical material for freezing, storing and thawing;
coupling a support member having a handle to the container, the support member being configured to support a weight of the container in response to the support member being received on a support structure of a temperature control unit and the interior receiving the biopharmaceutical material; and
supporting the container within the temperature control unit on the support member to allow the contact area to be exposed to a heat transfer surface separate from the support member to allow heat transfer between the heat transfer surface and the biopharmaceutical material.

19. The method of claim 18 further comprising receiving the support member on a support structure of a transportation cart to allow the container to be received in a channel of the transportation cart.

20. The method of claim 18 further comprising configuring the container to allow the container to be compressed within a width dimension of the support member.

21. The method of claim 18 further comprising connecting a port to the container to provide fluid communication between the interior of the container and an exterior of the container.

22. The method of claim 18 wherein the container comprises at least one aperture configured to receive at least one post projecting from the support member.

23. The method of claim 18 further comprising forming the container of at least one of a flexible material and a semi-rigid material.

* * * * *

UNITED STATES PATENT AND TRADEMARK OFFICE
CERTIFICATE OF CORRECTION

PATENT NO. : 6,996,995 B2
DATED : February 14, 2006
INVENTOR(S) : Voute et al.

Page 1 of 1

It is certified that error appears in the above-identified patent and that said Letters Patent is hereby corrected as shown below:

Column 10,
Line 10, insert -- to -- after "unit".

Signed and Sealed this

Twenty-third Day of May, 2006

JON W. DUDAS
*Director of the United States Patent and Trademark Office*